United States Patent [19]
Hardy et al.

[11] Patent Number: 5,162,235
[45] Date of Patent: Nov. 10, 1992

[54] METHOD FOR ASSESSING DISTILLATE FUEL STABILITY BY OXYGEN OVERPRESSURE

[75] Inventors: Dennis R. Hardy, Alexandria, Va.; Erna J. Beal, Fort Washington; Jack C. Burnett, Oxon Hill, both of Md.

[73] Assignee: The United States of America as represented by the Secretary of the Navy, Washington, D.C.

[21] Appl. No.: 371,782

[22] Filed: Jun. 27, 1989

[51] Int. Cl.$^5$ .................. G01N 5/00; G01N 25/54; G01N 33/22

[52] U.S. Cl. .................. 436/177; 436/139; 436/141; 436/156; 436/160; 44/903

[58] Field of Search .................. 436/60, 139-143, 436/156, 160, 174, 177; 73/61.2, 61.3; 44/903

[56] References Cited

PUBLICATIONS

Hiley, R. W. et al., "Third international conference on stability and handling of liquid fuels: Conference proceedings: vol. 2" The Institute of Petroleum, London, UK 1988 p. 456, Report No.: Conf-880905-vol. 2.

Primary Examiner—James C. Housel
Assistant Examiner—David Redding
Attorney, Agent, or Firm—Thomas E. McDonnell; Barry A. Edelberg

[57] ABSTRACT

Reactions leading to insoluble sediments formation in distillate fuel are accelerated by forcing oxygen into solution in the fuel at pressures of between about 90 and 110 psig and then stressing the fuel under conditions of accelerated storage at temperatures of between about 40° C. to 100° C. The method then makes use of gravimetric determination of the total insolubles formed. The stability of the fuel over a period of time as well as its comparative stability to other fuels can then be predicted from the amount of insolubles formed. The method can be carried out by using a specialized pressure vessel.

14 Claims, 1 Drawing Sheet

METHOD FOR ASSESSING DISTILLATE FUEL STABILITY BY OXYGEN OVERPRESSURE

BACKGROUND OF THE INVENTION

1. Field of the Invention

This invention relates to a device and method to assess and predict the stability of stored fuels.

2. Description of the Prior Art

As available petroleum crudes continue to decrease in quality and the amount of catalytically cracked stock used in middle-distillate fuels increases, there is a need for an accelerated stability test which is capable of reliably assessing and predicting the long term storage stability of middle distillate fuels such as Grade No. 1D and Grade No. 2D diesel fuels.

Currently used methods for fuel storage stability assessment assume Arrhenius-like behavior for typical fuels being oxidized in the temperature region from 20° C. to 95° C. under laboratory accelerated tests (Hardy, Dennis R., Hazlett, Robert N., Giannini, R., and Strucko, R., "Stability Measurements of Commercial Marine Fuels from a Worldwide Survey" *SAE Technical Paper Series,* No. 860895, 1986). For each 10° C. rise in temperature, there is an approximate doubling in reaction rate. However, these methods suffer from a variety of drawbacks (Hardy, D. R., Beal, E. J., Hazlett R. N., and Burnett, J. C., "Assessing Distillate Fuel Storage Stability By Oxygen Overpressure," Proceedings of the Third International Conference on Stability and Handling of Liquid Fuels, 1988). Some tests take too long. For example, lower temperature bottle tests are generally good indicators of storage stability of a particular fuel. However, meaningful results require storage at 43° C. for between 12 and 18 weeks. On the other hand, bottle storage tests at temperatures of 80° C. and above can be completed in a reasonably short time. But, these tests are generally poor indicators of actual ambient fuel reactions that lead to insoluble products.

Another test widely used as a rapid assessment of fuel storage oxidative stability is the ASTM D2274 method. This method accelerates the oxidation of fuels (and thus decreases the time required for fuel stability measurement) by bubbling oxygen through the fuel. It is not a good predictor of storage stability for freshly refined middle-distillate fuels that contain any catalytically cracked stocks. The recommended fuel incubation time of 16 hours is too short for many fuels and leads to misleading results and very small amounts of total insolubles which are hard to quantify. Because of these results, this test allows a potentially unstable fuel to pass the test.

SUMMARY OF THE INVENTION

Accordingly, it is an object of this invention to provide a device for assessing fuel stability by oxygen overpressure.

It is also an object of the invention to provide a method for assessing and predicting the long term storage stability of middle distillate fuels that is predictive for up to four years.

It is a further object of the invention to provide a rapid and precise method for predicting the long term storage of middle distillate fuels.

It is a further object of the invention to provide a device and method for accelerating the formation of fuel insoluble products in middle distillate fuels which may be generated during ambient storage of such fuels.

These and additional objects of the invention are accomplished by purposely accelerating the reactions leading to insoluble sediments formation by forcing oxygen into solution in the fuel at a pressure of between about 90 and 110 psig and then stressing the fuel under conditions of accelerated storage at temperatures between about 40° to 100° C. The amount of insolubles formed is measured by gravimetric determination. The stability of the fuel over a period of time as well as its comparative stability to other fuels can then be predicted from the amount of insolubles formed.

BRIEF DESCRIPTION OF THE DRAWINGS

A more complete appreciation of the invention will be readily obtained by reference to the following Detailed Description of the Invention and the accompanying drawings in which like numerals in different figures represent the same structures or elements, wherein.

DETAILED DESCRIPTION OF THE INVENTION

Figure 1:
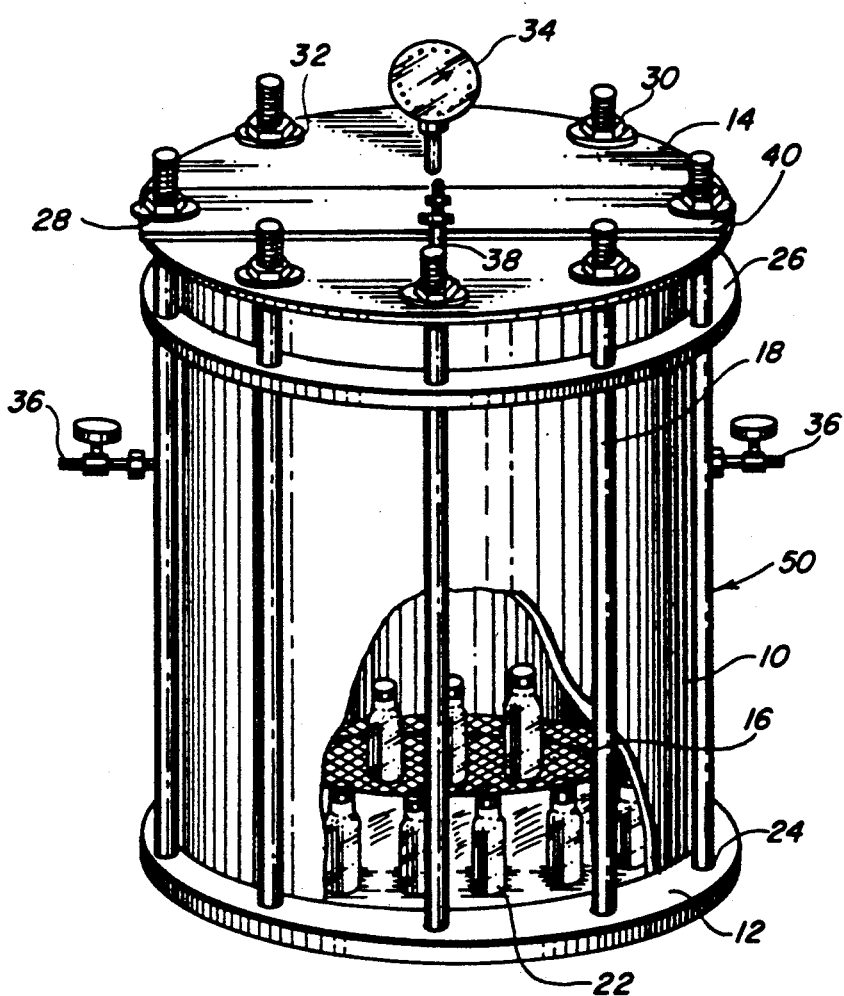
FIG. 1 is a three dimensional view of the Low Pressure Reactor (LPR).

The present invention is a rapid and precise method of predicting the fuel stability of middle distillate fuels for up to four years at ambient conditions. Furthermore, the present invention is suitable for freshly refined fuels or fuels already in storage, regardless of whether stabilizer additives have been added.

All of the reagents used in the method of this invention should be reagent grade chemicals that conform to the specifications of the Committee on Analytical Reagents of the American Chemical Society where such specifications are available. Other grades may be used, but the reagent must be of sufficiently high purity to permit its use without lessening the accuracy of the determination.

The fuel must be above its cloud point and thoroughly mixed prior to sampling. The fuel must also be kept from light in a non-reactive container for laboratory handling. It is preferable to use a borosilicate glass container with some type of light protection. It is most preferable to use amber borosilicate glass containers for this purpose.

The fuel should be pre-filtered prior to sampling. This can be accomplished by pulling the fuel sample through a non-reactive filter, such as a glass fiber filter. Any means of pulling the fuel through the filter may be used, but it is preferable to place at least two glass filters in a filter funnel and use a water aspirator or vacuum pump as a source of vacuum. A water aspirator is most preferable. The filter(s) used should be a workable size, with between about 40 to 80 mm in diameter preferred and about 47 mm being most preferred. The filter funnel should be large enough to accommodate the filter used.

The amount of fuel to be pre-filtered as a sample should be enough to give consistent and correct results but not so much as to hinder the analysis and waste reagents. A sample size of 90 to 120 ml is preferred, with a 100 ml sample being most preferred. The sample containers should be non-reactive, large enough to hold the sample, protect the sample from light, and should have some means for the sample to "breathe" in the container. Preferably, borosilicate glass containers capable of holding about 100 ml of sample but not more than about 200 ml of sample with a perforated top closure are used. In the most preferred embodiment, a 125 ml brown borosilicate glass bottle with a top closure of aluminum foil perforated with small holes is used.

The sample containers must be cleaned before use. Any means that will remove adherent insolubles can be used, but it is preferable to rinse out the sample containers with a solvent mixture. Rinsing out the containers with a solution consisting of approximately equal volumes of toluene, acetone, and methanol (TAM) followed by an ionized or distilled water wash, a mildly alkaline or neutral laboratory detergent wash and another ionized or distilled water wash is most preferred. The containers should be dried following any cleaning. Placing the containers in an oven at about between 100° and 120° C. until they are dry is preferred, with an oven at about 110° C. being most preferred.

Whether one or more fuels are being sampled, each fuel should have enough samples to give consistent results and each run (whether one or more fuels) should also have at least one blank. These blanks are empty sample containers. It is preferable to have between about two or three samples, with three samples and one blank being most preferred. All the samples are placed in the sample containers.

Next, the sample containers are placed in a pressure vessel. The vessel must be such that it can hold the samples and provide both the temperatures and pressures required by the method. In the preferred embodiment, the vessel may be a Test Method D525 oxidation apparatus and it may also be the Low Pressure Reactor (LPR) provided by the present invention. The LPR is most preferred.

Referring to FIG. 1, the LPR comprises a pressure chamber (50) and a removable top plate (14). The pressure chamber (50) comprises a cylinder (10) and a bottom plate (12). Preferably, the cylinder (10) is made of a material able to withstand temperatures of up to about 150° C. and pressures of up to about 200 kPa. In the most preferred embodiment, the cylinder (10) is constructed of steel pipe able to withstand a test pressure of about 2000 kPa. The cylinder (10) wall is about 0.65 cm in thickness.

The cylinder (10) may be any size, depending on the number of sample containers (22) to be placed in the LPR. Preferably, the LPR is large enough to hold at least 11 sample containers (22) on one level, requiring an inside diameter of at least about 22 centimeters and a height of at least about 10 centimeters. An LPR large enough to hold about 22 sample containers (22) is most preferred, requiring an inside diameter of about 22.23 centimeters and a height of about 26.67 centimeters. In this most preferred embodiment, 11 sample containers (22) are placed on the bottom of the LPR, a wire screen (16) of sufficient size to cover the sample containers (22) is placed on top of the sample containers (22), and another layer of 11 sample containers (22) is placed on top of the wire screen (16).

A top plate (14) rests on top of the cylinder (10). This top plate (14) should be constructed of 304 stainless steel plate. The thickness of the top plate (14) should be such that the top plate (14) can withstand pressures of up to about 2000 kPa. Most preferably, the top plate (14) is about 0.97 centimeters in thickness. The top plate (14) should be large enough to cover the top of the cylinder (10).

Similarly, a bottom plate (12) rests under the cylinder (10). It should meet the same requirements as for the top plate (14).

A means of securing the bottom plate (12) to the cylinder (10) should be provided. Preferably, the bottom plate (12) is securely and permanently attached to the bottom of the cylinder (10). In the most preferred embodiment, the bottom plate (12) is welded to the bottom of the cylinder (10).

Figure 2:
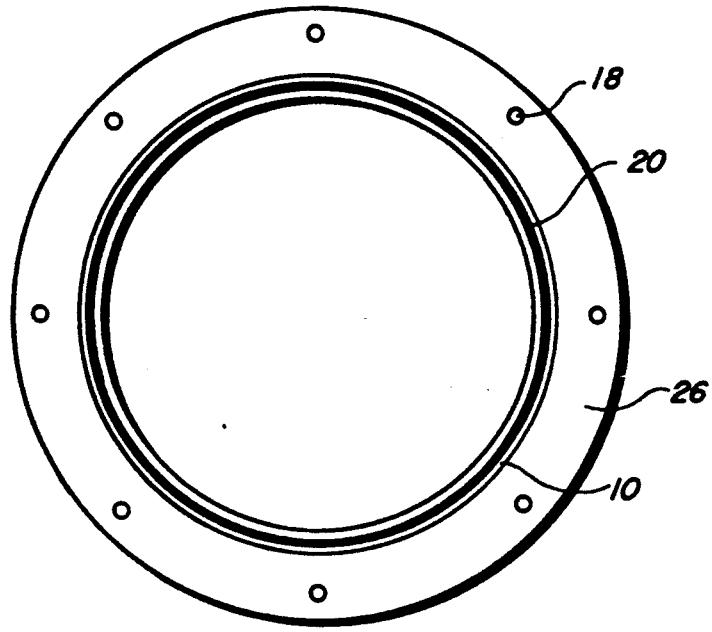
FIG. 2 is a top view of the LPR.

Similarly, a means of securing the top plate (14) to the top of the cylinder (10) must be provided. Preferably, the top plate (14) should not be permanently attached so that the top plate (14) can be temporarily attached to the cylinder (10), forming a pressure tight seal. In the most preferred embodiment, the top plate (14) is secured through a number of threaded rods (18) and, referring to FIG. 2, an O ring (20) mounted along the top of the cylinder (10). This O ring should be a material that is both flexible and able to withstand the temperatures of the method. A neoprene O ring is preferred. Eight threaded rods (18), about 1.6 cm in diameter, run from top plate (14) to bottom plate (20). The threaded rods (18) are constructed from American Standard Class B bolt material with an ultimate strength of about 60,000 psi. At the bottom plate (12), they are threaded and welded into eight evenly spaced threaded holes (24) in the bottom plate (12), each hole (24) placed so that the threaded rods (18) run alongside the cylinder (10). The threaded rods (18) then run to the top plate (14), passing through a ring guide (26) which is welded to the cylinder (10) and to which the threaded rods (18) themselves are welded. This provides extra stability for the threaded rods (18). At the top plate (14), the threaded rods (18) pass through holes (28) that line up with the holes (24) in the bottom plate (12). Furthermore, the rubber O ring (20) rests in a groove in the top of the cylinder (10). In the pressure tight position, the top plate (14) is securely attached to the cylinder (10) by bolting the top plate (14) to the cylinder (10) using nuts (30) threaded onto the eight threaded rods (18). Washers (32) may be placed between the nuts (30) and the top plate (14) for greater closure strength and more even pressure. The contact of the O ring (20) against the top plate (14) and the pressure of the top plate (14) against the cylinder (10) provides a pressure tight seal. This pressure tight seal can be further improved by providing a metal bar (40) running from bolt to bolt across the center of the top plate. The LPR should be equipped with a gauge (34) to measure pressure within the LPR.

A means for introducing gas into and of exhausting gas from the cylinder (10) should also be provided. Preferably, gas inlet(s)/outlet(s) and a safety relief valve (to reduce the risk of explosion) are provided. In the most preferred embodiment, two gas inlets/outlets (36) and a safety relief valve (38) are attached through the cylinder (10), although the gas inlet/outlet and safety relief valve could be placed at any position.

Prior to placing the sample containers in the pressure vessel, the pressure vessel should be preheated to the reaction temperature and kept at this temperature throughout the method. The reaction temperature should be between about 40° to 100° C., with between about 85° to 95° C. being preferred and 90° C. being most preferred. Any means of heating the pressure vessel may be used, such as ovens, integral heating coils, water baths, heating jackets and the like. It is preferable to use a heating means that can provide uniform heating, can be operated between about 40° and 100° C. to within about 1° C. and can hold the pressure vessel. It is most preferable to use an explosion proof oven.

After placing the samples in the heated pressure vessel, the heated pressure vessel is closed and secured so that the pressure vessel is pressure tight. The heated pressure vessel is then connected to an oxygen source so that the heated pressure vessel can be pressurized with oxygen. Preferably, this is accomplished by connecting an oxygen-containing tank to the heated pressure vessel via a regulator capable of delivering up to between about 790 and 810 kPa (99 to 101 psig). It is most preferable to use a preset regulator set at about 800 kPa (100 psig). The oxygen in the tank must be pure enough so that the reaction will occur. Preferably, the oxygen is between about 99 and 100% pure, with about 99.5% pure being most preferred.

Next, the heated pressure vessel is pressurized with oxygen. Preferably, the heated pressure vessel is pressurized to between about 750 and 850 kPa (95 to 105 psig) with about 800 kPa being most preferred. As soon as the heated pressure vessel is pressurized, the pressure is released and the process of pressurizing/depressurizing repeated. Again, the heated pressure vessel is pressurized and held at the pressure for enough time to precipitate insolubles (called the aging period). The reaction time for the aging period is pre-determined, depending on the type of fuel storage stability assessment being performed. For example, if one is testing the fuel to predict its stability over a period of time, one will have to calculate the time required to simulate fuel storage at ambient conditions taking into account the reaction temperature. These calculations can be made from known standards in the industry, such as the Annual Book of ASTM Standards. If one is testing various fuels to obtain their relative stabilities, one should keep the samples under oxygen pressure and reaction temperature until the amount of insolubles formed over time is a linear relationship. Preferably, between about 14 and 18 hours is sufficient, with about 16 hours being most preferred.

After the aging period, the temperature and pressure of the pressure vessel is measured and recorded. If the pressure has dropped below the initial pressure, then the test is invalid and the procedure will have to be repeated with new samples. If valid, then the pressure is released at a rate of not more than about 10 psig per minute and the pressure vessel opened and the heat source removed. The sample containers are removed and allowed to cool to about ambient room temperature. Preferably, the sample containers are protected from light during this stage.

Next, the insolubles that have formed in the samples are removed from the samples. Any means of completely removing the insolubles may be used, but a combination filtration/organic solvent wash is preferred. Most preferably, the sample is filtered through a pre-weighed non-reactive filter, such as a glass fiber filter similar to the one used earlier, using a means of suction, such as a vacuum. The sample is rinsed twice with an organic hydrocarbon solvent with a residue upon evaporation of less than about 0.001% and a boiling point between about 35° and 100° C. Preferably, the hydrocarbon solvent is selected from the group comprising hexanes, heptane, isooctane, and petroleum ether. The filter holder should also be washed. The sample container should be washed, too, with an appropriate solvent. Preferably, TAM solvent is used and the washes are placed in a pre-weighed container so that the washes may be evaporated. Most preferably, the pre-weighed containers are aluminum weighing dishes. A hot plate capable of evaporating about 10 ml of toluene in between about 10 and 25 minutes is used to evaporate.

Next, the insolubles are weighed but must be dry before weighing. It is best to dry the insolubles and their containers in a drying oven at about 110° C. until they are dry. In the most preferred embodiment, this is about four hours. It is also preferable to cool the insolubles to ambient temperature before weighing.

By gravimetric determination, the total amount of insolubles in a weight/volume ratio can be calculated, taking into account the weight of any containers or filters used.

As previously mentioned, this weight/volume ratio can be utilized in various ways. One can rate the stability of fuels against other fuels or against a fuel standard by comparing the insoluble weight/volume ratios of various fuels. The lower the weight/volume ratio, the more stable the fuel.

Also, one can predict the stability of a fuel in terms of amount of insolubles formed by calculating the required time, temperature and oxygen pressure necessary to simulate prolonged storage of a fuel. For example, the table below lists the variable test conditions for predicting the stability of a fuel over 40 months if the method is used with an oxygen pressure of 800 kPa.

| Temperature (°C.) | Time of Method |
| --- | --- |
| 40 | 32 days |
| 60 | 8 days |
| 80 | 48 hours |
| 90 | 24 hours |
| 100 | 12 hours |

If the method of the present invention predicts that, over 40 months, a fuel will develop no more than the maximum amount of insolubles (weight/unit volume of fuel) permitted by an industry specification, that fuel will be stable during 40 months of storage. The maximum amount of insolubles permitted in a fuel will depend on the usage envisioned for that fuel. As an example, one industry specification is set forth in Navy Ship Technical Manual S9086-HB-STM-000, Chapter 233, "Diesel Engines", and Navy Ship Technical Manual S9086-HC-STM-000, "Marine Gas Turbines").

Having described the invention, the following examples are given to illustrate specific applications of the invention. These specific examples are not intended to limit the scope of the invention described in this application.

EXAMPLE

A mini-round robin was conducted using four fuel samples that were blends of 30% catalytically cracked light cycle oil and 70% straight run fuel. A fifth fuel sample was a naval distillate (NATO F-76) fuel. All reagents used were reagent grade chemicals that conformed to the specifications of the American Chemical Society where such specifications were available. The bulk fuels were above their cloud points and thoroughly mixed.

For each sample, two glass fiber filters, 47 mm in diameter, were placed in a filter funnel. 100 ml of the fuel (the fuel sample) was then pre-filtered using a water aspirator vacuum. The filtered fuel sample was placed in a sample container. The sample container was a 125 ml brown borosilicate glass bottle with a top closure of aluminum foil perforated with small holes for breathing. The sample containers were prepared for use by rinsing thoroughly with TAM solvent (a filtered solution of equal volumes of toluene, acetone, and methanol) followed by water. Then, the sample containers were washed with a mildly alkaline laboratory detergent, rinsed with distilled water and dried in an oven at 110° C.

Three samples were prepared using the above method for each fuel. In addition, three empty sample containers were used as blanks. After putting the samples in the sample containers, all sample containers were placed in the pressure vessel.

The pressure vessel was placed in an explosion proof oven capable of being operated between 40° and 100° C. to within 1° C. and capable of holding the pressure vessel. The oxygen cylinder secondary regulator was set to deliver 800 kPa (absolute) (100 psig) and the pressure vessel was connected to the oxygen cylinder via the preset regulator. The oxygen in the tank was 99.5% pure and the cylinder had two stage regulators capable of delivering up to 1600 kPa (200 psig). The secondary regulator was calibrated against standards to deliver 790 to 810 kPa (99 to 101 psig). Once the tank was connected, the pressure vessel was slowly pressurized to about 800 kPa (100 psig). The pressure was then slowly released and the pressurization repeated. Again, the pressure was slowly released. For a third and final time, the vessel was pressurized to 790 to 810 kPa (99 to 101 psig) as preset on the secondary regulator.

The pressure vessel gas inlet valve was closed and the oven set so that a pressure vessel temperature of 90° C. was maintained for 16 hours.

While the samples were "aging", disposable aluminum weighing dishes (two for each sample, including the blank) capable of holding 47 mm diameter filters and 30 ml of solvent were soaked in fresh, clean TAM solvent for several minutes followed by drying in a drying oven at 110° C. Two hours after removal from the oven, one dish was firmly nested inside the other for each sample and blank to be run. Two dry glass fiber filters were placed in each "dish assembly" and the entire assembly of two filters and two aluminum dishes was weighed to the nearest 0.1 mg on an analytical balance.

At the end of this aging period, the temperature was measured and recorded. If the pressure had dropped below 800 kPa (absolute) (100 psig) the test would have been invalid. The pressure was slowly released and the vessel opened. The sample containers were removed from the vessel and allowed to cool to ambient room temperature (about 25° C.) in the dark for at least an hour.

For each sample, the two filters from a pre-weighed filter/dish assembly were placed in a filter funnel with suction applied. The contents of the sample container were completely filtered. After the sample container was empty and the filters were dry, (a) the vacuum was relieved, (b) the sample was rinsed with 25 ml of filtered hydrocarbon solvent and poured into the filter holder, and (c) the solvent pulled through the filter with the aspirator. Steps (a) through (c) were then repeated. Finally, the filter holder was washed with filtered hydrocarbon solvent from a rinse bottle.

Next, the sample container was carefully rinsed with two consecutive 15 ml portions of TAM solvent, rinsing the entire inner surface of the container with solvent. Both solvent rinses were poured into the upper dish of the nested aluminum weighing dish assembly, which was then placed on a hot plate and slowly evaporated for 10 minutes just to dryness.

The two test filters were then placed in the upper dish of the assembly. At this point, all sample and blank filters and weighing dish assemblies were put in a drying oven at 110° C. for at least four hours. They were removed from the oven and allowed one hour to cool to ambient temperature (25° C.). Each two filter/two weighing dish assembly was weighed to the nearest 0.1 mg.

The total insolubles in mg/100 ml was calculated as follows:

$$TI = B - C - D$$

$$D = (E - F)/2$$

where:
TI = total insolubles of an individual sample
B = weight in mg of an individual sample after filtering of aged sample
C = weight in mg of an individual sample before filtering of aged sample
D = blank correction for an individual sample
E = the sum of the two blanks after filtering
F = the sum of the two blanks before filtering
The results were as follows:

| Fuel Code | Lab 1 | Lab 2 | Lab 3 | Lab 4 | Average |
|---|---|---|---|---|---|
| 1 | 1.1 | 1.7 | 0.9 | 1.0 | 1.2 |
| 2 | 1.7 | 1.4 | 1.9 | 1.0 | 1.5 |
| 3 | 2.8 | 3.7 | 3.3 | 4.0 | 3.5 |
| 4 | 3.4 | 5.1 | 3.2 | 5.1 | 4.2 |
| 5 | 10.9 | 14.0 | 12.8 | 11.6 | 11.6 |

Obviously, many modifications and variations of the present invention are possible in light of the above teachings. It is therefore to be understood that within the scope of the appended claims, the invention may be practiced otherwise than as specifically described.

What we claim is:

1. A method for determining the stability of a distillate fuel over a period of time, comprising:
   pre-determining the reaction time for the fuel;
   extracting a fuel sample to be tested;
   heating the fuel sample under pressure in a substantially pure oxygen atmosphere for the reaction time;
   cooling the fuel sample and depressurizing the fuel sample to ambient pressure in normal atmosphere;
   determining the amount of insolubles precipitated in the sample gravimetrically; and correlating the amount of insolubles to the stability of the fuel.

2. A method as described in claim 1 wherein the fuel sample is heated and pressurized in a pressure vessel.

3. A method as described in claim 2 wherein the step of pressurizing the fuel sample comprises the steps of:
   pressurizing the pressure vessel to between about 750 and 850 kPa of oxygen pressure;
   releasing the oxygen pressure;
   re-pressurizing the vessel to between about 750 and 850 kPa of oxygen pressure;
   re-releasing the oxygen pressure;
   re-pressurizing the vessel to between about 750 and 850 kPa of oxygen pressure;
   holding the vessel at that pressure until all insolubles precipitate;

re-releasing the oxygen pressure.

4. A method as described in claim 1 wherein the fuel sample size is between about 90 and 120 ml.

5. A method as described in claim 4 wherein the fuel sample size is about 100 ml.

6. A method as described in claim 1 wherein the fuel sample is heated to between about 85° and 95° C.

7. A method as described in claim 6 wherein the fuel sample is heated to about 90° C.

8. A method as described in claim 2 wherein the pressure vessel is heated an explosion proof oven.

9. A method as described in claim 1 wherein the substantially pure oxygen is between about 99 and 100% pure.

10. A method as described in claim 9 wherein the substantially pure oxygen is 99.5% oxygen.

11. A method as described in claim 2 wherein the substantially pure oxygen is delivered to the pressure vessel by means of a regulator capable of delivering between about 790 to 810 kPa.

12. A method as described in claim 11 wherein the regulator is preset to deliver about 800 kPa.

13. A method as described in claim 1 wherein the reaction time required for substantially all insolubles to precipitate is between about 14 to 18 hours.

14. A method as described in claim 13 wherein the reaction time required for substantially all insolubles to precipitate is about 16 hours.

* * * * *